United States Patent
Kolter et al.

(10) Patent No.: US 8,597,679 B2
(45) Date of Patent: Dec. 3, 2013

(54) FINE-PARTICLE CROSSLINKED POLYVINYLPYRROLIDONE AS TABLET DISINTEGRANT

(75) Inventors: Karl Kolter, Limburgerhof (DE); Bernhard Fussnegger, Kirrweiler (DE); Michael Kerber, Weinheim (DE); Harald Armbruster, Limburgerhof (DE); Hubertus Folttmann, Heidelberg (DE); Ralf Widmaier, Mannheim (DE); Marianna Pierobon, Ludwigshafen (DE)

(73) Assignee: BASF SE (DE)

( * ) Notice: Subject to any disclaimer, the term of this patent is extended or adjusted under 35 U.S.C. 154(b) by 1427 days.

(21) Appl. No.: 12/094,516

(22) PCT Filed: Dec. 11, 2006

(86) PCT No.: PCT/EP2006/069514
§ 371 (c)(1),
(2), (4) Date: May 21, 2008

(87) PCT Pub. No.: WO2007/071580
PCT Pub. Date: Jun. 28, 2007

(65) Prior Publication Data
US 2008/0299191 A1    Dec. 4, 2008

(30) Foreign Application Priority Data

Dec. 21, 2005 (EP) .................................. 05112607
Dec. 23, 2005 (EP) .................................. 05112963

(51) Int. Cl.
*A61K 9/20* (2006.01)
(52) U.S. Cl.
USPC .......................................... 424/464; 424/501
(58) Field of Classification Search
None
See application file for complete search history.

(56) References Cited

U.S. PATENT DOCUMENTS

| 4,658,002 | A | 4/1987 | Tschang et al. |
| 6,329,334 | B1 | 12/2001 | Bertleff et al. |
| 6,677,417 | B2 | 1/2004 | Meffert et al. |
| 2005/0232988 | A1* | 10/2005 | Venkatesh et al. ............ 424/464 |

FOREIGN PATENT DOCUMENTS

| EP | 0 177 812 | 4/1986 |
| EP | 1 036 839 | 9/2000 |
| WO | WO-03/032978 | 4/2003 |
| WO | WO-03/072084 | 9/2003 |
| WO | WO-2005/105049 | 11/2005 |

OTHER PUBLICATIONS

Bühler, V. "Polyvinylpyrrolidone Excipients for Pharmaceuticals," Springer Verlag Berlin Heidelberg, pp. 128-131, 2005.

* cited by examiner

*Primary Examiner* — Hasan Ahmed
(74) *Attorney, Agent, or Firm* — Novak Druce Connolly Bove + Quigg LLP

(57) ABSTRACT

Use of crosslinked polyvinylpyrrolidone with an average particle size of 5-60 μm and a hydration capacity of greater than 7 g/g as tablet disintegrant.

21 Claims, No Drawings

FINE-PARTICLE CROSSLINKED POLYVINYLPYRROLIDONE AS TABLET DISINTEGRANT

CROSS REFERENCE TO RELATED APPLICATIONS

This application is a national stage application of PCT/EP2006/069514, filed Dec. 11, 2006, which claims benefit of European Patent Application No. 05112607.6, filed Dec. 21, 2005, and European Patent Application No. 05112963.3, filed Dec. 23, 2005; the entire contents of all are hereby incorporated by reference.

The present invention relates to the use of fine-particle crosslinked polyvinylpyrrolidone with an average particle size of from 5 to 60 μm and a hydration capacity greater than 7 g/g as tablet disintegrant.

The use of disintegrants for improving the disintegration and dissolution rate of tablets has been generally known for a long time.

One of the most commonly used disintegrants in this connection is crosslinked polyvinylpyrrolidone. Such crosslinked polyvinylpyrrolidones are commercially available, for example Kollidon® CL types from BASF Aktiengesellschaft or as Polyplasdone® XL types from ISP Investments Inc.

Crosslinked polyvinylpyrrolidone is mainly employed in relatively coarse form as tablet disintegrant (Kollidon CL in the region of 120 μm and Polyplasdone XL in the region of 130 μm), the average particle size being greater than 100 μm. Although the large particle size leads to a good disintegrant effect, it has numerous disadvantages such as a rougher tablet surface on storage under moist conditions, low resistance to crushing, decrease in the resistance to crushing on storage under moist conditions, inhomogeneous tablet mixing and tendency to segregation in the tablet mixture. An additional factor is that the coarse disintegrant particles cause a gritty and unpleasant mouthfeel.

It has always been the general opinion to date that the disintegrant effect correlates with the particle size. Accordingly, smaller particles ought always to result in a considerably reduced disintegrant effect (see V. Buehler, "Polyvinylpyrrolidone Excipients for Pharmaceuticals", p. 128 et seq., Springer Verlag Berlin Heidelberg, 2005. Thus, the disintegrant effects of Polyplasdone XL 10 (particle sizes in the region of 30 μm) and of Kollidon CL-M (particle sizes in the region of 5 μm) are considerably smaller. Thus, to achieve a particular disintegrant effect with these small-particle products, much higher concentrations are necessary, which is in turn disadvantageous because higher costs result and the tablets become more moisture-sensitive. It is very often impossible even by increasing the concentration to achieve a disintegration as fast as on use of coarse-particle crosslinked polyvinylpyrrolidone.

U.S. Pat. No. 6,677,417 discloses the use of crosslinked polyvinylpyrrolidones with particle sizes of >400 μm to 1500 μm as tablet disintegrants.

It was an object of the present invention to find tablet disintegrants which help to avoid the described disadvantages.

Accordingly, the use defined at the outset has been found. The crosslinked polyvinylpyrrolidone disintegrants used according to the invention have an average particle size of 5-60 μm, preferably 10-50 μm and particularly preferably 15-40 μm. The hydration capacities are greater than 7.0 g/g, preferably greater than 7.5 g/g and particularly preferably greater than 8.0 g/g, and may be up to 12.0 g/g.

The hydration capacity is determined by the following method:

2 g of polymer are weighed into a centrifuge tube and left to swell with 40 ml of water for 15 minutes. This is followed by centrifugation at 2000 rpm for 15 minutes, and the supernatant liquid is poured off and the sample is reweighed.

$$\text{Hydration capacity} = \frac{\text{final weight} - \text{tare}}{\text{initial weight}}$$

(see also V. Buehler, "Polyvinylpyrrolidone Excipients for Pharmaceuticals", p. 132 et seq., Springer Verlag Berlin Heidelberg, 2005)

Such crosslinked polyvinylpyrrolidones can be prepared by a polymerization process which is known per se and is referred to as popcorn polymerization. The popcorn polymerization is carried out by known processes, e.g. as precipitation polymerization or by bulk polymerization. An example of a known procedure is one where—as described in EP-B-0 177 812—the popcorn polymerization is started by heating a mixture of 99.6 to 98.8% by weight N-vinylpyrrolidone and 0.4 to 1.2% by weight of a compound having at least two ethylenically unsaturated double bonds, as crosslinker, to a temperature in the range from 100 to 150° C. in the absence of oxygen and polymerization initiators.

The compounds employed as crosslinkers comprise at least two ethylenically unsaturated double bonds in the molecule. Particularly suitable examples are alkylene-bisacrylamides such as methylenebisacrylamide and N,N'-acryloylethylenediamine, N,N'-divinylethyleneurea, N,N'-divinylpropyleneurea, ethylidenebis-3-(N-vinyl-pyrrolidone), N,N'-divinyldiimidazolyl(2,2')butane and 1,1'-bis(3,3'-vinylbenzimidazolyl-2-one)1,4-butane. Examples of other suitable crosslinkers are alkylene glycol di(meth)acrylates such as ethylene glycol diacrylate, ethylene glycol dimethacrylate, tetraethylene glycol acrylate, tetraethylene glycol dimethacrylate, diethylene glycol acrylate, diethylene glycol methacrylate, aromatic divinyl compounds such as divinylbenzene and divinyltoluene, and vinyl acrylate, allyl acrylate, allyl methacrylate, divinyldioxane, pentaerythritol triallyl ether, and mixtures of the crosslinkers. The crosslinker which is preferably employed is N,N'-divinylethyleneurea.

The crosslinkers are used in amounts of from 0.1 to 10, preferably 1 to 4,% by weight, based on the monomers employed in the polymerization.

This polymerization can be initiated by the presence of small amounts of sodium hydroxide solution or potassium hydroxide solution. Within a short time there is formation of a polymerizable popcorn polymer which, on addition of further N-vinyl-pyrrolidone and continued addition of the crosslinker, starts and completes the popcorn polymerization without an induction period, the particle size of the resulting popcorn polymers being controlled according to the invention by passing a stream of inert gas preferably into the monomers introduced into the polymerization vessel even before starting the popcorn polymerization. However, the passing in of the stream of inert gas is started at the latest during the polymerization induction period, and the stream of inert gas is passed through the reaction mixture throughout the popcorn polymerization.

In order to carry out the popcorn polymerization without solvent, i.e. in bulk, the introduced monomer is rendered inert by passing in nitrogen and then heated to a temperature in the range from 100 to 200, preferably 150 to 180° C. It is advantageous to continue to pass a gentle stream of nitrogen through the monomers even during the polymerization. Exclusion of oxygen is also achieved by polymerizing the mixture under a pressure which is below atmospheric pressure and at which the monomers boil. However, the popcorn polymerization can be carried out under reduced pressure with simultaneous passing in of an inert gas. Depending on the amount of monomer employed and the chosen temperature, the mixture polymerizes within 1 to 20 hours. The popcorn polymer is obtained therefrom in yields of more than 90% in the form of a powder.

However, precipitation polymerization in water is preferred for preparing the popcorn polymers. The concentration of the monomers is in this case expediently chosen so that the reaction mixture can be stirred satisfactorily throughout the reaction. If the monomer concentration in water is too high, e.g. 95% by weight, the polymer grains become tacky so that stirring becomes more difficult than in more dilute aqueous solution. In order to carry out the reaction in conventional stirred vessels, the monomer concentrations are chosen, based on the aqueous mixture, to be for example about 5 to 30, preferably 10 to 20,% by weight. If more powerful stirrers are available, the monomer concentration of the aqueous solution may also be increased to 50% by weight, and if appropriate above this. It may be expedient in some cases to start the popcorn polymerization with a relatively concentrated solution and then to add water for dilution during the reaction.

The popcorn polymerization is preferably carried out at pH values above 6 in order to avoid any possible hydrolysis of the monomers. The pH can be adjusted by adding small amounts of bases such as sodium hydroxide or ammonia or of the usual buffer salts such as sodium carbonate, sodium bicarbonate or sodium phosphate. Exclusion of oxygen can be achieved if appropriate by heating the mixture to be polymerized to boiling and additionally passing a stream of inert gas through the reaction mixture to control the particle size of the popcorn polymers.

The particle size of the popcorn polymers is in this case controlled by the amount of the stream of inert gas which is passed through the polymerization solution. If little inert gas is supplied to the reaction mixture, coarse popcorn polymers usually result, but if a large amount of inert gas flows through the polymerization solution, finer popcorn polymers result. It is not possible to indicate for each individual case the exact conditions for adjusting a particular particle size for the popcorn polymers, depending on various limiting conditions such as, for example, vessel size, temperature and pressure. The correct amount of inert gas which must be passed through the reaction mixture in the individual case can easily be found by a few simple experiments. As indicated above, the amounts of inert gas to be passed through the reaction mixture are in the range from 0.01 to 100, preferably 0.1 to 30, l of inert gas/l of reaction mixture/h.

Noble gases such as helium, neon or argon can be used as inert gas. Carbon dioxide is also suitable. Nitrogen is preferably used.

It is further possible to add to the reaction mixture, in order to remove dissolved oxygen completely, small amounts—e.g. 0.1 to 1% by weight, based on the monomer mixture—of a reducing agent such as sodium sulfite, sodium pyrosulfite, sodium dithionite, ascorbic acid or mixtures of the reducing agents. In a preferred embodiment, the popcorn polymerization takes place in the presence of sodium dithionite as reducing agent.

The polymerization temperature may be varied within a wide range, e.g. from about 20 to 200, preferably 50 to 150° C.

In a particularly preferred embodiment of the precipitation polymerization, a water-soluble comonomer, part of the crosslinker, water, and, if appropriate, a buffer and a reducing agent are heated in a stream of inert gas until the first polymer particles become evident. Then—if desired—a mixture, which has previously been rendered inert by blowing in nitrogen, of one or more of the abovementioned comonomers and the remaining crosslinker and, if appropriate, water as diluent is added over the course of 0.2 to 5 hours. This procedure has the advantage that the popcorn polymerization takes only a short time.

The popcorn polymers usually result in a yield of about 90 to >99% of the theoretical yield. They can be isolated from the aqueous suspension by filtration or centrifugation with subsequent washing with water and drying in conventional dryers such as circulating air or vacuum drying oven, paddle dryer, tumble dryer, fluidized bed dryer or flash dryer. The popcorn polymers are insoluble in water and all solvents and moreover swell only slightly therein. The swollen volumes in water are in the range from 8 to 10 l/kg.

Popcorn polymers suitable according to the invention are commercially available as Divergan® types from BASF Aktiengesellschaft.

The process is managed in such a way that the average particle size of the dried polymers is in the range from 5 µm to 60 µm and the hydration capacity is greater than 7 g/g. The particle sizes can be determined by light scattering using a Malvern Mastersizer.

These polymers can be blended very homogeneously into tablet mixtures and thus lead to considerably reduced standard deviations of the tablet disintegration times. The tablet surface is considerably smoother even on storage under moist conditions.

The polymers of the invention are particularly suitable for tablets which disintegrate quickly in the mouth, called fast dispersible or fast meltable tablets, because, in contrast to the coarse disintegrants, the mouthfeel generated is not sandy but in fact very soft and pleasant.

They are equally advantageous for tablets which are left to disintegrate in a glass of water before being taken. In such cases there is no formation of a granular sediment; on the contrary, a fine suspension results.

An additional factor is that they can be mixed with very large amounts of water or organic solvents without becoming moist or resulting in a paste or a slurry. This property is particularly advantageous for wet granulation in a mixer, especially if relatively high disintegrant concentrations and relatively high binder concentrations are also to be used. Surprisingly, the polymers of the invention do not lose their disintegrant effect through moistening and drying, i.e. they can be included in the granulation, and the tablets nevertheless disintegrate quickly. For this reason too, they are particularly suitable for wet granulation.

The disintegrants used according to the invention are normally employed in amounts of from 0.5 to 50% by weight, preferably 1 to 10% by weight, based on the tablet weight.

The disintegrants used according to the invention are suitable in principle for producing tablets for all classes of active pharmaceutical ingredients. They are further suitable also for producing dietary supplements in tablet form.

The disintegrants used according to the invention are preferably suitable for producing fast-disintegrating tablets. Fast disintegrating means that the tablets disintegrate completely within 10 to 120 seconds in water at 20° C.

The disintegrants used according to the invention are particularly suitable for producing tablets which disintegrate quickly in the mouth.

Properties of the polymers used according to the invention (polymers 1, 2) and of the comparative products:

|  | Kollidon CL | Kollidon CL-M | Polyplasdone XL 10 | Polymer. 1 | Polymer 2 |
| --- | --- | --- | --- | --- | --- |
| Hydration capacity [g/g] | 4.4 | 4.0 | 4.6 | 8.0 | 8.1 |
| Average particle size [μm] | 120 | 5 | 29 | 19 | 21 |

USE EXAMPLES

Placebo Tablets
Composition of the Tablets with a Disintegrant Concentration of 6%:

| Ludipress LCE | 467.50 mg |
| --- | --- |
| Disintegrant | 30.00 mg |
| Mg stearate | 2.50 mg |
| Tablet weight | 500.00 mg |

All the ingredients were passed through a 0.8 mm sieve and mixed in a Turbula mixer (from Bachofen, Switzerland) for 10 min. Tableting took place in an eccentric press (Korsch EKO, from Korsch, Berlin) with 30 strokes/min using a 12 mm punch (beveled). The compressive force was 18 kN.

The following tablet properties were achieved:

|  | No disintegrant | Kollidon CL | Kollidon CL-M | Polyplasdone XL | Polyplasdone XL 10 | Polymer 1 |
| --- | --- | --- | --- | --- | --- | --- |
| Disintegration | 433 | 70 | 291 | 73 | 127 | 67 |
| Rel. standard deviation of disintegration (%) | 15.7 | 14.5 | 13.9 | 14.0 | 6.3 | 6.5 |
| Resistance to crushing (N) | 165 | 145 | 194 | 148 | 161 | 178 |
| Friability (%) | 0.19 | 0.11 | 0.05 | 0.16 | 0.12 | 0.05 |

Test of the Stability of the Tablets at 23° C./65% r.h for 7 Days:

| Tablet with Kollidon CL: | 6.5 |
| --- | --- |

Test of the Stability of the Tablets at 23° C./65% r.h for 7 Days:

| Tablet with Kollidon CL: | 6.5 |
| --- | --- |
| Tablet with polymer of ex. 1 | 4 |

Criteria for Assessing the Tablet Surface:

| 1 | smooth |
| --- | --- |
| 2 | small irregularities on the tablet surface |
| 3 | small irregularities/rough tablet surface |
| 4 | noticeable irregularities/incipient pockmarking |
| 5 | slight pockmarking |

-continued

| 6 | intermediate pockmarking |
| --- | --- |
| 7 | severe pockmarking |
| 8 | severe pockmarking/tablet brittle and spongy |

Pain Tablets
Composition of the Tablet with a Disintegrant Concentration of 2.7% by Weight:

| Acetylsalicylic acid powder | 250.00 mg |
| --- | --- |
| Paracetamol cryst | 250.00 mg |
| Caffeine gran. 0.2-0.5 | 50.00 mg |
| Kollidon 30 | 27.50 mg |
| Disintegrant | 16.00 mg |
| Mg stearate | 5.00 mg |
| Tablet weight | 598.50 mg |

Firstly, the three active ingredients were mixed in a Diosna mixer and moistened with a 20% aqueous Kollidon 30 solution. The moist composition was then passed through a screen with a mesh width of 0.8 mm and dried in a thin layer on a tray at room temperature for 24 h. These granules were mixed with the disintegrant and magnesium stearate passed through a 0.8 mm sieve and mixed in a Turbula mixer (from Bachofen, Switzerland) for 10 min. Tableting took place in an eccentric press (Korsch EKO, from Korsch, Berlin) with 30 strokes/min using a 12 mm punch (beveled). The compressive force was 18 kN.

The following tablet properties were achieved:

|  | No disintegrant | Kollidon CL | Kollidon CL-M | Polyplasdone XL | Polyplasdone XL 10 | Polymer of ex. 1 |
|---|---|---|---|---|---|---|
| Disintegration (min:s) | 70:40 | 9:13 | 18:15 | 13:03 | 19:04 | 7:36 |
| Resistance to crushing (N) | 165 | 93 | 120 | 97 | 106 | 149 |
| Friability (%) | 0.38 | 0.38 | 0.20 | 0.41 | 0.42 | 0.25 |

Test of the Stability of the Tablets at 23° C./85% r.h for 7 Days:

| Kollidon CL: | 6.5 |
|---|---|
| Crospovidone No. 1 | 3 |
| Hydration capacity | 8.0 g/g |

Vitamin C Tablets

Composition of the Tablet with a Disintegrant Concentration of 3.2% by Weight:

| Vitamin C 90 (Roche) | 480.00 mg |
|---|---|
| Avicel PH 102 | 96.06 mg |
| Disintegrant | 19.20 mg |
| Mg stearate | 4.32 mg |
| Tablet weight | 599.58 mg |

All the ingredients were passed through a 1.0 mm sieve and mixed in a Turbula mixer (from Bachofen, Switzerland) for 10 min. The tableting took place on a rotary press (Korsch PH 106, from Korsch, Berlin) at 40 rpm using a 12 mm punch (beveled). The compressive force was 18 kN.

The following tablet properties were achieved:

|  | No disintegrant | Kollidon CL | Kollidon CL-M | Polyplasdone XL | Polyplasdone XL 10 | Polymer of ex. 1 |
|---|---|---|---|---|---|---|
| Disintegration (min:s) | 11:29 | 3:57 | 6:12 | 4:53 | 6:00 | 4:54 |
| Resistance to crushing (N) | 141 | 114 | 207 | 131 | 144 | 200 |
| Friability (%) | 0.21 | 0.21 | 0.12 | 0.14 | 0.15 | 0.11 |

| Kollidon CL: | 6 |
|---|---|
| Crospovidone No. 1 | 2.5 |
| Hydration capacity | 8.0 g/g |

Orally Disintegrating Loratadine Tablet

Composition of the Tablet with a Disintegrant Concentration of 8.0%:

| Loratadine | 10.0 mg |
|---|---|
| Mannitol | 100.0 mg |
| Erythritol | 73.0 mg |
| Disintegrant | 16.0 mg |
| Mg stearate | 1.0 mg |
| Tablet weight | 200.0 mg |

All the ingredients were passed through a 0.8 mm sieve and mixed in a Turbula mixer (from Bachofen, Switzerland) for 10 min. The tableting took place on a rotary press (Korsch PH 106, from Korsch, Berlin) at 40 rpm using an 8 mm punch (beveled). The compressive force was 15 kN.

The following tablet properties were achieved:

| Disintegration in the mouth: | 40 s |
|---|---|
| Mouthfeel: | very pleasant, slightly cooling, not granular |
| Resistance to crushing: | 50 N |

Rapidly Disintegrating Acetylsalicylic Acid Tablet

Composition of the Tablet with a Disintegrant Concentration of 8.0% by Weight:

| Acetylsalicylic acid | 100.0 mg |
|---|---|
| Mannitol | 60.0 mg |
| Avicel PH 101 | 53.5.0 mg |
| Disintegrant | 35.0 mg |
| Mg stearate | 1.5 mg |
| Tablet weight | 250.0 mg |

All the ingredients were passed through a 0.8 mm sieve and mixed in a plowshare mixer (from Lödige) for 5 min. Tableting took place in a rotary press (Korsch PH 106, from Korsch, Berlin) at 30 rpm using a 10 mm punch (beveled). The compressive force was 16 kN.

The following tablet properties were achieved:

| Resistance to crushing: | 70 N |
|---|---|
| Disintegration in a glass of water (200 ml): | 60 s, appearance: fine suspension |

We claim:

1. A composition comprising a crosslinked polyvinylpyrrolidone produced by popcorn polymerization with an average particle size of 5-60 μm and a hydration capacity greater than 7 g/g wherein the composition is utilized as a tablet disintegrant.

2. The composition according to claim 1, where the average particle size is from 10 to 50 μm.

3. The composition according to claim 1, where the average particle size is from 15 to 40 μm.

4. The composition according to claim 1, where the hydration capacity is greater than 7.5 g/g.

5. The composition according to claim 1, where the hydration capacity is greater than 8.0 g/g.

6. A tablet comprising the composition of claim 1, wherein the crosslinked polyvinylpyrrolidone produced by popcorn polymerization is present in concentrations of from 0.5 to 50% by weight based on the total weight of the tablet.

7. The tablet according to claim 6, comprising the crosslinked polyvinylpyrrolidone produced by popcorn polymerization in concentrations of from 1.0 to 10% by weight.

8. A tablet which rapidly disintegrates in the mouth comprising the composition of claim 1 wherein the crosslinked polyvinylpyrrolidone produced by popcorn polymerization is present in concentrations of from 1.0 to 10% by weight.

9. The tablet which rapidly disintegrates in the mouth according to claim 8, comprising from 20 to 95% by weight of a sugar alcohol.

10. The composition according to claim 2, where the hydration capacity is greater than 7.5 g/g.

11. The composition according to claim 3, where the hydration capacity is greater than 7.5 g/g.

12. The composition according to claim 2, where the hydration capacity is greater than 8.0 g/g.

13. The composition according to claim 3, where the hydration capacity is greater than 8.0 g/g.

14. A tablet comprising the composition of claim 2 wherein the crosslinked polyvinylpyrrolidone produced by popcorn polymerization is present in concentrations of from 0.5 to 50% by weight based on the total weight of the tablet.

15. A tablet comprising the composition of claim 3 wherein the crosslinked polyvinylpyrrolidone produced by popcorn polymerization is present in concentrations of from 0.5 to 50% by weight based on the total weight of the tablet.

16. A tablet comprising the composition of claim 4 wherein the crosslinked polyvinylpyrrolidone produced by popcorn polymerization is present in concentrations of from 0.5 to 50% by weight based on the total weight of the tablet.

17. A tablet comprising the composition of claim 5 wherein the crosslinked polyvinylpyrrolidone produced by popcorn polymerization is present in concentrations of from 0.5 to 50% by weight based on the total weight of the tablet.

18. A tablet which rapidly disintegrates in the mouth comprising the composition of claim 2 wherein the crosslinked polyvinylpyrrolidone produced by popcorn polymerization is present in concentrations of from 1.0 to 10% by weight.

19. A tablet which rapidly disintegrates in the mouth comprising the composition of claim 3 wherein the crosslinked polyvinylpyrrolidone produced by popcorn polymerization is present in concentrations of from 1.0 to 10% by weight.

20. A tablet which rapidly disintegrates in the mouth comprising the composition of claim 4 wherein the crosslinked polyvinylpyrrolidone produced by popcorn polymerization is present in concentrations of from 1.0 to 10% by weight.

21. A tablet which rapidly disintegrates in the mouth comprising a disintegrant which comprises a crosslinked polyvinylpyrrolidone produced by popcorn polymerization with an average particle size of 5-60 μm and a hydration capacity greater than 7 g/g, wherein the crosslinked polyvinylpyrrolidone is obtained by a process comprising:
   a) polymerizing a reaction mixture comprising N-vinylpyrrolidone and a crosslinker comprising a compound having at least two ethylenically unsaturated double bonds in the absence of oxygen and polymerization initiators; and
   b) passing an inert gas stream into the reaction mixture to form crosslinked polyvinylpyrrolidone with an average particle size of 5-60 μm.

* * * * *